(12) United States Patent
Sosnowska-Turek et al.

(10) Patent No.: US 11,045,507 B2
(45) Date of Patent: Jun. 29, 2021

(54) ***BIFIDOBACTERIUM ANIMALIS* AMT30 STRAIN AND THE COMPOSITION CONTAINING THE STRAIN OF *BIFIDOBACTERIUM ANIMALIS* AMT30**

(71) Applicants: Ewelina Sosnowska-Turek, Olsztyn (PL); Jaroslaw Turek, Olsztyn (PL)

(72) Inventors: Ewelina Sosnowska-Turek, Olsztyn (PL); Jaroslaw Turek, Olsztyn (PL)

( * ) Notice: Subject to any disclaimer, the term of this patent is extended or adjusted under 35 U.S.C. 154(b) by 11 days.

(21) Appl. No.: 16/281,651

(22) Filed: Feb. 21, 2019

(65) Prior Publication Data
US 2020/0268812 A1    Aug. 27, 2020

(51) Int. Cl.
*A61K 35/745* (2015.01)
*A23L 33/135* (2016.01)
*C12R 1/01* (2006.01)
*C12N 1/20* (2006.01)
*A61K 9/06* (2006.01)
*A61K 35/00* (2006.01)

(52) U.S. Cl.
CPC .......... *A61K 35/745* (2013.01); *A23L 33/135* (2016.08); *A61K 9/06* (2013.01); *C12N 1/205* (2021.05); *A23V 2002/00* (2013.01); *A23Y 2300/21* (2013.01); *A61K 2035/115* (2013.01); *C12R 2001/01* (2021.05)

(58) Field of Classification Search
CPC ....... A61K 35/745; A61K 9/06; A23L 33/135; C12R 1/01; C12R 2001/01
See application file for complete search history.

(56) References Cited

U.S. PATENT DOCUMENTS

| | | | |
|---|---|---|---|
| 2009/0117056 | A1 | 5/2009 | Hodal, Jr. et al. |
| 2016/0338361 | A1 | 11/2016 | Smittle et al. |

FOREIGN PATENT DOCUMENTS

| | | | |
|---|---|---|---|
| CA | 2918430 | A1 | 1/2015 |
| EP | 1840205 | | 10/2007 |
| EP | 3048165 | A1 | 7/2016 |
| PL | 208421 | | 4/2011 |
| PL | 212096 | | 8/2012 |
| PL | 229020 | | 5/2018 |
| WO | 2012101500 | A1 | 8/2012 |
| WO | 2016205394 | A1 | 12/2016 |

OTHER PUBLICATIONS

Jungersen et al, The Science behind the Probiotic Strain *Bifidobacterium animalis* subsp. *lactic BB-12*, 2014, Microorganisms, vol. 2, pp. 92-110 (Year: 2014).*
Bender, A Dictionary of Food and Nutrition, 3rd ed. 2009, definition of "bulking agent," retrieved from oxford reference https://www.oxfordreference.com/view/10.1093/acref/9780199234875.001.0001/acref-9780199234875-e-910?rskey=r6CEXs&result=1 (Year: 2009).*
Bender, A Dictionary of Food and Nutrition, 3rd ed. 2009, definition of "non-starch polysaccharide," retrieved from oxford reference https://www.oxfordreference.com/view/10.1093/oi/authority.20110803100238239 (Year: 2009).*
European Search Report completed Apr. 10, 2018, from EP Application No. EP 17 46 0068, 4 sheets.
Polish Search Report dated Jul. 18, 2017, from Polish Application No. P.419333, 2 sheets.
Krieg N.R., et al., Gram-dodatnie paleczki o nieregularnej morfologii, Bergey's Manual of Determinative Bacteriology, Wiliams and Wilkins, 1984, vol. 2, coverpage, plus pp. 1418-1434.
Müller G., The Basics of Food Microbiology WNT, 1983, Warszawa; pp. 155-158.
S. Ehrstrom, Lactic acid bacteria colonization and clinical outcome after probiotic supplementation in conventionally treated bavterial vaginosis and vulvovaginal candidiasis, Microbes and Infection 12 (2010) 691-699.
Schlegel H.G., General Microbiology 2000, PWN, Warszawa), pp. 349-351.
Hoover D.G., Bifidobacteria: activity and potential benefits, Food Technol., 1993, 47, 120-124.
Gibson G.R., Wang X, Regulatory effects of bifidobacteria on the growth of other colonic bacteria, J. Appl. Bacteriol., 1994, 77, 412-420.
Gomes A.M. P., Malcata F. X., *Bifidobacterium* sp. and Lactobacillus acidophilus: biological, biochemical, technological and therapeutical properties relevant for use as probiotics, 1999, Trends in Food Science and Technology, 10, 139-157.
Biedrzycka E., et al., Siwicki A.K., 2007, Shaping the micro ecosystem of gastrointestinal tract. Development control of gastrointestinal system in newborn mammals, ed. Zabielski R., Wydawnictwo Rolne i Lesne, 5, 126-140.
Boris S., et al., Adherence of Human Vaginal Lactobacilli to Vaginal Epithelial Cells and Interaction with Uropathogens, Infection and Immunity, May 1998, vol. 66, No. 5, pp. 1985-1989.
Servin A.L., Antagonistic activities of lactobacilli and bifidobacteria against microbial pathogens, 2004, FEMS Microbiology Reviews, vol. 28, 405-440.
Haberek M., et al., Candidiasis of the vagina and the vulva (VVC), Zakażenia, 2007, vol. 2, 79-81.

(Continued)

*Primary Examiner* — Ruth A Davis
(74) *Attorney, Agent, or Firm* — Myers Wolin, LLC

(57) ABSTRACT

Disclosed herein is a new strain of *Bifidobacterium animalis* AMT30 bacteria deposited by the number PCM B/00109 as well as composition for production of creams and ointments, parapharmaceutical, pharmaceutical, food preparations/products and food and water additives for humans and animals, consisting of the new strain of bacteria, medium and bulking agent distinguished by that the bacterial strain contains *Bifidobacterium animalis* AMT30, PCM B/00107 in amount of $10^1$ to $10^{13}$ of colony forming units cfu/ml-g. The composition may contain one or more strains of *Lactobacillus plantarum* bacteria.

2 Claims, No Drawings

(56) References Cited

OTHER PUBLICATIONS

Biegańska M.J., et al., Infection of Candida fungi in animals, Mikologia Lekarska, 2008, vol. 15, No. 3, 155-159.

Mijač V.D., et al., Hydrogen peroxide producing lactobacilli in women with vaginal infections, 2006, European Journal of Obstetrics & Gynecology and Reproducive Biology, 129, 69-76.

Markiewicz L.H., et al., Rapid molecular identification and characteristics of Lactobacillus strains. Folia Microbiol., 2010, 55 (5), 481-488.

Anonymous: "Sktadniki PROteinBIOTIC", QuickFit Probiotics Supplements, Jul. 16, 2017 (Jul. 16, 2017), XP002779845, Retrieved from the Internet: URL:https://www.facebook.com/quickfitprobiotics/photos/a.1232119256933830.1073741828.1209862485826174/1232178663594556/?type=3&theater, [retrieved on Apr. 9, 2018], *the whole document*.

Anonymous: "Wartosci odzywcze i sktadproduktu", BioticFoods, XP002779846, Retrieved from the Internet: URL: http://bioticfoods.eu/wartosci-odzywcze-i-sklad-produktu/, [retrieved on Apr. 9, 2018], *the whole document*.

M Gagnon: "In vitro inhibition of *Escherichia coli* 0157:H7 by bifidobacterial strains of human origin", International Journal of Food Microbiology, vol. 92, No. 1, Apr. 1, 2004 (Apr. 1, 2004), pp. 69-78, XP055465577, NL, ISSN: 0168-1605, DOI: 10.1016/j.ijfoodmicro.2003.07.010, *the whole document*.

Gopal P K et al, "In vitro adherence properties of Lactobacillus rhamnosus DR20 and Bifidobacterium lactis DR10 strains and their antagonistic activity against an enterotoxigenic *Escherichia coli*", International Journal of Food Microbiology, vol. 67, No. 3, Aug. 5, 2001 (Aug. 5, 2001), pp. 207-216, XP027287759, Elsevier BV, NL, ISSN: 0168-1605, [retrieved on Aug. 5, 2001], *the whole document*.

http://www.natuhouse-polska.pl/wgrane_pliki/mivinat_probiotic.pdf, Dec. 19, 2014.

http://www.chr-hansen.com/en/probiotic-supplements-and-infant-formula/cards/product-cards/bifidobacterium-animalis-subsp-lactis-bb-12, Feb. 10, 2015.

Communication under Rule 71(3) EPC Intention to grant dated Sep. 18, 2020, from EP Application No. EP 17 460 068.4, 26 sheets.

Claire L. Vernazza, et al., "Carbohydrate preference, acid tolerance and bile tolerance in five strains of Bifidobacterium", 2006 The Society for Applied Microbiology, Journal of Applied Microbiology 100 (2006), pp. 846-853.

* cited by examiner

BIFIDOBACTERIUM ANIMALIS AMT30 STRAIN AND THE COMPOSITION CONTAINING THE STRAIN OF BIFIDOBACTERIUM ANIMALIS AMT30

FIELD OF THE INVENTION

The subject matter of the invention is a new strain of *Bifidobacterium animalis* AMT30 and a composition containing new strain of *Bifidobacterium animalis* AMT30.

BACKGROUND

*Bifidobacterium* genus (lat. "*bifidus*"—bifurcate), first isolated and described in 1899-1900 by Tissier, is formed by Gram-positive rods of irregular morphology (Krieg N. R., Holt J. G., *Bergey's Manual of Determinative Bacteriology*, Wiliams and Wilkins, 1984, Vol. 2). They reach sizes in a range of 0.5-1.3×1.5-8 µm. They can be plain or split. The rods have different shapes depending on the species and the strain as well as on environment in which they live. The bacterial cells freshly isolated from gastrointestinal tract or multiplying media, under optimal incubation condition usually have characteristic form of X, Y or Y, but also have clavate and spatula shape of rounded ends generally. They occur singly or in groups, do not move and do not form endospores.

Bifidobacteria require strict anaerobic growth conditions (Müller G., The Basics of Food Microbiology WNT, 1990, Warszawa). They proliferate at a temperature of 37-41° C. and in an environment having pH in a range of 6.0-7.0. Bifidobacteria produce basic metabolites as lactic acid and acetic acid. They have activity of intracellular fructose-6-phosphate phosphoketolase (FKF6F) enzyme. This enzyme is involved in specific enzyme pathway of glucose metabolism—called "*bifidus* pathway". It is an enzyme characteristic for *Bifidobacterium* genus, used to identify the type of bacteria.

0.7-millimeter crypts, which are densely packed pockets in epithelium of large intestine mucous membrane, are the natural environment of bifidobacteria (Saloff-Coste C. J., *Bifidobacteria*. Danone World Newsletter, 1997, 16, 1-9; Schlegel H. G., *General Microbiology* 2000, PWN, Warszawa). The bacterial cells adhere to the microvilli of enterocytes surface as well as to the mucus covering the epithelial cells, without causing damage to the enterocytes. Bifidobacteria perform many advantageous functions. Bifidobacteria are involved in digestion processes and metabolism as well as synthesis of vitamins B1, B2, B6, B12, as well as nicotinic and folic acids. They protect the digestive tract from pathogens colonization and inhibit the growth of putrefactive and pathogenic bacteria. (Hoover D. G., *Bifidobacteria: activity and potential benefits*, Food Technol., 1993, 47, 120-124; Gibson G. R., Wang X, *Regulatory effects of bifidobacteria on the growth of other colonic bacteria*, J. Appl. Bacteriol., 1994, 77, 412-420; Gomes A. M. P., Malcata F. X., *Bifidobacterium ssp. and Lactobacillus acidophilus: biological, biochemical, technological and therapeutical properties relevant for use as probiotics*, 1999, Trends in Food Science and Technology, 10, 139-157):

Development and final stabilization of the digestive tract microecosystem are formed as a result of the balance of the microflora of digestive tract, the physiological interaction of the organism, diet or other external factors (Biedrzycka E., Markiewicz L. H, Bielecka M., Siwicki A. K., 2007, *Shaping the micro ecosystem of gastrointestinal tract. Development control of gastrointestinal system in newborn mammals*, ed. Zabielski R., Wydawnictwo Rolne i Leśne, 5, 126-140). The way of feeding is an important and decisive factor that differentiates the microflora of infants. Microflora of infants who are breastfed is dominated in 95% by bifidobacteria even within first week whereas *Lactobacillus* bacteria constitute less than 1% of the population. The ratio of bacteria population of *Bifidobacterium* family to bacteria from Enterobacteriaceae family is 1000:1. In contrast, the microflora of not breastfed infants is characterized by the longer presence of larger (by the number) population of relatively anaerobic bacteria, including Enterobacteriaceae family as well as Enterococcus family; the ratio of the population of bifidobacteria to Enterobacteriaceae bacteria is 1:10. Bifidobacteria do not produce gas and irritating products of fermentation process and thus reduce the risk of intestinal colic and other dietary disorders. Furthermore, lactic and acetic acid that are produced by the bacteria reduce the pH of the large intestine content inhibiting the growth of pathogenic bacteria such as: *Escherichia coli, Shigella, Clostridium perfringens*. Thus attention should be paid to very important role played by bifidobacteria in proper growth of gastrointestinal tract microsystem in the initial stage and to the fact that later in life the number of bifidobacteria population is significantly reduced, which results in acceleration of ageing process, health and well-being deterioration.

Bacteria of *Bifidobacterium animalis* strain, with proven biocidal properties against pathogenic bacteria and fungi, supplementation of human and animal diet is considered reasonable.

The natural microflora of the genitourinary system is a kind of protective microecosystem (Boris S., Suárez J. A., Vázquez F., Barbès C., *Adherence of Human Vaginal Lactobacilli to Vaginal Epithelial Cells and Interaction with Uropathogens*, Infection and Immunity, May 1998, Vol. 66, No. 5, 1985-1989). It is dominated by the *Lactobacillus* bacteria, which can be described as "hygiene guard". They feed on glycogen of vaginal epithelium autolysis undergoing cells and the products of their metabolism acidify the environment, preventing the growth of pathogenic bacteria. Pathogens of genitourinary tract originate mainly from gastrointestinal tract; they colonize first urethra, and then expand into the urinary bladder, causing "bacteriuria" (Servin A. L., *Antagonistic activities of lactobacilli and bifidobacteria against microbial pathogens*, 2004, FEMS Microbiology Reviews, Vol. 28, 405-440). These microorganisms are characterized by the virulence, which makes them more resistant to effective, in normal conditions, defence mechanisms of host. One of the most common causes of vaginal ecosystem disorders is antibiotic treatments, especially with broadspectrum antibiotics. (Haberek M., Mierzyński R., Leszczyńska-Gorzelak B., Oleszczuk J., *Candidiasis of the vagina and the vulva (VVC)*, Zakażenia, 2007, Vol. 2, 78-81). They destroy not only pathogenic microflora, but also friendly one. Fungi usually inhabit the environment without protection, causing inflammation and de-acidification, which promotes growth of other pathogenic microorganisms. Prophylactic and therapeutic cultures of *Lactobacillus*, widely studied and already used in inflammations of genitourinary tract, do not show antagonism against *Candida*, which mostly infect genital tract (Haberek M., Mierzyński R., Leszczyńska-Gorzelak B., Oleszczuk J., *Candidiasis of the vagina and the vulva (VVC)*, Zakażenia, 2007, Vol. 2, 78-81). Fungi are acidophilic organisms, therefore lactic acid produced by *Lactobacillus* bacteria and decreased pH level is not inhibitory factor for them. This fact is confirmed by observed in practice growth of yeasts and mould in fermented products of both vegetable and animal origin.

In recent years an increase in the number of *Candida* fungi infections in livestock and farm animals as well as in so-called small animals has been observed (Biegańska M. J., *Infection of Candida fungi in animals*, Mikologia Lekarska, 2008, Vol. 15, No. 3, 155-159). *Candida albicans* is the pathogen most frequently isolated from dogs, cats, horses and cattle, other species of *C. guilliermondii, C. krusei, C. tropicalis* and *C. parapsilosis* are also mentioned. Clinical symptoms observed throughout candidosis in animals resemble by their location and escalation, fungal infections described in humans. Infections of gastrointestinal tract, genital tract, urinary tract, mammary gland as well as skin are predominant in animals. Nose and paranasal sinuses candidosis are relatively fewer. There are also few cases of organ and systemic candidosis, although the latter usually concern animals with impaired immunity. *Candida albicans* and so-call non-albicans *Candida* cause serious systemic infection, in extreme cases leading to the death of the animal.

According to the inventions patented in Poland, PL212096, PL208421 and patent application P.406050, strains of *Bifidobacterium* genus may play an essential role in increasing the body's resistance to all kinds of infections, including intestinal infections. They have ability to survive for a certain period of time in the intestinal tract at pH 5.5-6.5, producing and isolating glutamine, participate in ammonia conversion, thus may influence on metabolic processes in the gastrointestinal tract. They may also affect the immune and nervous systems. Similar observation was the basis for the patents granting for *Bifidobacterium infantis* Pl. 212096, *Bifidobacterium longum* PL208421, *Bifidobacterium lactis* UA84513 or EP1840205.

SUMMARY

The invention relates to the new strain of *Bifidobacterium animalis* AMT30 and composition containing new strain of *Bifidobacterium animalis* AMT30 or composition containing bacteria of *Lactobacillus plantarum* AMT14 and/or *Lactobacillus plantarum* AMT12 and medium, distinguished by outstanding probiotic properties, especially emphasising antagonism against fungi and bacteria potentially pathogenic and/or pathogenic for humans and animals.

Analyzing the unique properties of the *Bifidobacterium animalis* AMT30 strain one must conclude that it can be used to produce creams and ointments, preparations/ parapharmaceutical, pharmaceutical and food products, food and water additives for humans and animals as well as deodorant formulation. *Bifidobacterium animalis* AMT30 strain ability to inhibit the growth and then to reduce the population of *Candida* fungi is unique, especially when such properties are not found in other bacteria. Clinical studies on women with various genital tract diseases such as: bacterial infections, candidosis, trichomoniasis prove this fact.

The strains of *Lactobacillus* producing $H_2O_2$, isolated from both healthy and sick women, could protect against bacterial infections but they were ineffective in case of *Candida blastomyces* and vagina *trichomonas* (*Trichomonas vaginalis*) infections (Mijač V. D., Dukić S. V., Opayski N. Z., Dukić M. K., Ranin L. T., Hydrogen peroxide producing lactobacilli in women with vaginal infections, 2006, European Journal of Obstetrics & Gynecology and Reproductive Biology, 129, 69-76). This data confirm usefulness of probiotic *Bifidobacterium animalis* AMT30 bacteria application in fungal and bacterial infections treatment, Invention relates to the composition of *Bifidobacterium animalis* bacterial strains and bacterial strains of *Lactobacillus* genus.

Except the additional benefits concerning effects of lactic acid produced by these bacteria, they can protect bifidobacteria from the harmful effects of oxygen.

*Bifidobacterium animalis* AMT30 strain was deposited in the Polish Collection of Microorganism in the Institute of Immunology and Experimental Therapy of Polish Academy of Sciences in Wroclaw, deposit no B/00109.

DETAILED DESCRIPTION

Determination of Species Affiliation of the *Bifidobacterium animalis* AMT30.

The Identification of the Strain

The *Bifidobacterium animalis* AMT30 strain was isolated from the stool of an adult man. The strain was deposited under the Budapest Treaty in Polish Collection of Microorganisms (PCM) in the Institute of Immunology and Experimental Therapy of Polish Academy of Sciences (ul. Weigla 12, 53-114, Wroclaw, Poland). The deposit was lodged on 31 May 2016 and the number B/00109 was assigned.

Isolation of the *Bifidobacterium animalis* AMT30 Strain.

The strain isolation was performed using multistage screening method. The procedure of *Bifidobacterium* strain isolating was carried out on the basis of the culturing of tenfold dilutions of the material sample on the Garche's medium. The plates were incubated at 37° C. for 72 hours under anaerobic conditions (sealed jar with GasPac AN0025A, Oxoid, cartridge). Colonies of bacteria potentially belonging to the *Bifidobacterium* genus were multiplied on the liquid Garche's medium and were incubated at 37° C. for 24 hours under anaerobic conditions (sealed jar with GasPac AN0025A, Oxoid, cartridge).

Culturing and multiplying procedure was carried out until pure cultures of bacteria, classified by microscopic observation to *Bifidobacterium* genus, were obtained.

Confirmation of Isolated Strain Properties on the Genetic Level (RAPD and/or rep-PCR).

In order to isolate the genomic DNA reagent kit Bacterial & Yeast Genomic DNA Purification Kit from Eurx (Gdańsk) and purification procedure for Gram-positive bacteria were applied. The quality of the isolated DNA was checked by electrophoresis (1% agarose, 0.5×TBE, 100 V, 30 min.)

Isolates typing was performed applying rep-PCR method with the primer $(GTG)_5$ based on amplification technique as well as RAPD method (random amplification of polymorphic sections) with the primer S1 (CGACGTCATC). The procedure applied was identical to the previously described. (Markiewicz L. H., Biedrzycka E., Wasilewska E., Bielecka M. Rapid molecular identification and characteristics of *Lactobacillus* strains. Folia Microbiol., 2010, 55 (5), 481-488).

Identification of the Isolated *Bifidobacterium animalis* AMT30 Strain Using Sequencing of Encoding Gene 16S rRNA Fragment.

Identification of the isolated strain by sequencing of the fragment of the encoding gene 16S rRNA of at least 500 pairs was performed in the following stages:

1) DNA isolation from the colonies on Petri dishes.

Isolation of genetic material (DNA) from colonies of microorganisms supplied on Petri dishes was made. DNA was extracted applying CHELEX resin method (Biorad) and in the presence of the enzymes that break down the cell wall.

2) The PCR reaction with specific primers and PCR matrix sequencing.

In order to confirm the presence of bacteria in the examined sample PCR amplification of 16S rDNA fragments applying specific primers on DNA matrix isolated from colonies was made.

Positive result of amplification was obtained. PCR products were purified and then sequencing was performed using the following kit: BigDye Terminator Mix v3.1 and genetic analyzer ABI3730x1 as well as specific primers. Obtained readouts (readouts from specific starters for bacterial 16S rDNA: 27F and 1492R) were assembled into the corresponding contigs obtaining consensus sequence.

3) Comparison of the obtaining sequences with NCBI database

The obtained consensus sequences were compared with NCBI database—GeneBank using BLAST program.

Comparative analysis with DNA sequences deposited in the Gene Bank (NCBI) showed that the analyzed sequence is identical with the sequence of *Bifidobacterium animalis*.

In Vitro Study of Antagonistic Effect of *Bifidobacterium animalis* AMT30 Strain Against Pathogens of the Gastrointestinal Tract and Urogenital System.

atin). Pathogenic strains used in vitro studies came from the Institute of Animal Reproduction and Food Research of Polish Academy of Sciences in Olsztyn. While the strain of *Bifidobacterium animalis* AMT30 comes from the private collection of microorganism from PROBIOS ltd. Pathogenic strains were stored frozen at −80° C. and directly before the study were activated by twofold passage in hydrolyzed milk.

The shared cultures (examined samples) were inoculated using lyophilized *Bifidobacterium animalis* AMT30 strain at a level of $10^9$ colony forming units/ml (described hereinafter by commonly accepted abbreviation cfu/ml) as well as using active monoculture of pathogenic strain of the following species: *Escherichia coli* O157:H7, *Candida albicans* 637, *Candida krusei* 8 in an amount of $10^5$ cfu/ml.

The single strains of pathogenic microorganisms (*Escherichia coli* O157:H7, *Candida albicans* 637, *Candida krusei* 8) and monoculture of *Bifidobacterium animalis* AMT30 using inoculum level and liquid medium as in the shared culture were the control samples in the experiment.

The shared cultures as well as single ones were prepared in four parallel tubes in triplicate. Incubation was carried out under anaerobic conditions at 37° C. for 0 (inoculum determining blank test) 24, 48 and 72 hours. After the incubation the number of live cells of *Bifidobacterim animalis* AMT30 bacteria as well as the number of pathogens were determined in shared and control cultures using plate count test on appropriate agar media (Table 1).

The analysed material was diluted with 1% peptone water applying the method of serial tenfold dilutions and cultured on the bottom of Petrie dish, then the liquid agar medium at a temperature of 45° C. was poured. Directly after medium solidifying the plates were inverted upside down and incubated at 37° C. for 24 or 48 hours under aerobic or anaerobic conditions. Conditions of the culture are reported in Table 1. After the incubation, bacteria colonies of the shared cultures were counted and compared to the number of bacteria in the control cultures (single ones).

TABLE 1

Culture conditions of the analysed bacterial strains

| the strain type | Medium applied | incubation conditions |
|---|---|---|
| *Bifidobacterium animalis* AMT30 | Modified Garche's medium by Teroguchi et al. (1982). composition of multiplying medium:<br>Meat peptone 20 g/L<br>Yeast extract 2 g/L<br>L-cysteine hydrochloride 0.4 g/L<br>Lactose 10 g/L<br>Sodium acetate 6 g/L<br>$MgSO_4 \times 7H_2O$ 0.12 g/L<br>$Na_2 HPO_4 \times 12H_2O$ 2.5 g/L<br>$KH_2PO_4$ 2 g/L<br>distilled water 1000 mL<br>Garche's medium with agar (10 g/L) for quantitative determination of *Bifidobacterium animalis* AMT30 | 37° C./48 hours, anaerobic conditions created in sealed jar using GasPac cat. No. AN0025A cartridge, Oxoid. |
| *Escherichia coli* O157:H7 | Macconkey Agar (Merck, cat. no. 1054650500) | 37° C./24 hours, aerobic conditions |
| *Candida albicans* 637, *Candida krusei* 8 | Agar Sabouraud with chloramphenicol (BTL, cat no. P-0176) | 37° C./24 hours, aerobic conditions |

The study of antagonistic properties of *Bifodobacterium animalis* AMT30 strain against the following pathogens: *Escherichia coli* O157:H7 (enterohaemorrhagic strain), *Candida albicans* 637, *Candida krusei* 8 was performed on the shared cultures in hydrolyzed milk (10% milk regenerated from skimmed powdered milk, hydrolyzed using pancre- Overall reduction in the number of bacteria of *Escherichia coli* O157:H7 enterohaemorrhagic strain as well as *Candida albicans* 637 and *Candida krusei* 8 fungi during 72 hours of incubation of shared culture with *Bifidobacterium animalis* AMT30 was found in the in vitro studies. The results are presented in Table 2.

TABLE 2

Growth inhibition of pathogenic bacteria and fungi by *Bifidobacterium animalis* AMT30

| The strain Shared culture symbol | Inoculum number of cfu/mL | | 24 h of incubation number of cfu/mL | | 48 h of incubation number of cfu/mL | | 72 h of incubation number of cfu/mL | |
|---|---|---|---|---|---|---|---|---|
| | AMT30 | pathogen | AMT30 | pathogen | AMT30 | pathogen | AMT30 | pathogen |
| *Bifidobacterium animalis* AMT30 (monoculture) | $1.8 \times 10^9$ | | $2.4 \times 10^9$ | | $2.4 \times 10^9$ | | $2.1 \times 10^9$ | |
| *Escherichia coli* O157:H7 (monoculture) | | $2.9 \times 10^5$ | | $1.1 \times 10^9$ | | $8.8 \times 10^8$ | | $5.2 \times 10^8$ |
| *Candida albicans* 676 (monoculture) | | $6.1 \times 10^5$ | | $1.8 \times 10^7$ | | $1.5 \times 10^7$ | | $1.3 \times 10^7$ |
| *Candida krusei* 8 (monoculture) | | $1.2 \times 10^5$ | | $4.1 \times 10^8$ | | $2.9 \times 10^8$ | | $2.4 \times 10^8$ |
| *Bifidobacterium animalis* AMT30 + *Escherichia coli* O157:H7 | $1.8 \times 10^9$ | $2.9 \times 10^5$ | $2.7 \times 10^9$ | $1.8 \times 10^6$ | $2.5 \times 10^9$ | $3.1 \times 10^2$ | $2.1 \times 10^9$ | Abs* |
| *Bifidobacterium animalis* AMT30 + *Candida albicans* 676 | $1.8 \times 10^9$ | $6.1 \times 10^5$ | $2.7 \times 10^9$ | $1.1 \times 10^6$ | $3.1 \times 10^9$ | $1.1 \times 10^3$ | $2.8 \times 10^9$ | Abs* |
| *Bifidobacterium animalis* AMT30 + *Candida krusei* 8 | $1.8 \times 10^9$ | $1.2 \times 10^5$ | $2.5 \times 10^9$ | $1.4 \times 10^6$ | $3.6 \times 10^9$ | $7.3 \times 10^2$ | $3.8 \times 10^9$ | Abs* |

Abs*—absent in 1 ml of the culture shared with z *Bifidobacterium animalis* AMT30

Data obtained on the basis of inhibiting the growth of pathogenic strains lead to the conclusion, that the selected strain of *Bifidobacterium* genus has antagonistic properties against selected strains of pathogenic bacteria and fungi.

Determination of Survivability of *Bifidobacterium animalis* AMT30 Strain at Low pH as Well as in the Presence of Bile Salts The survivability of *Bifidobacterium animalis* AMT30 strain at low pH was determined by acidity reduction of *Bifidobacterium animalis* AMT30 culture being in stationary phase of growth to a pH value of 3. However, in the case of survivability determination of *Bifidobacterium animalis* AMT30 strain in the presence of bile salts, at the beginning pH of *Bifidobacterium animalis* AMT30 culture was raised to a value of 6, then bile salts in an amount of 3% of the culture were added. Determination of survivability of *Bifidobacterium animalis* AMT30 strain at low pH was performed before lowering the pH of the culture (control sample), just after lowering the pH of the culture to a value of 3, so called minute 0, and after 40 and 180 minutes of incubation at 37° C. under anaerobic conditions. The survivability of *Bifidobacterium animalis* AMT30 in the presence of bile salts was determined prior to bile salts addition (control sample), just after addition of bile salts, so called minute 0 and after 1, 3 and 6 hours of incubation at 37° C. under anaerobic conditions. The live cells of *Bifidobacterium animalis* AMT30 was determined in colony forming units (cfu/ml) following the pour plate method. The survivability of *Bifidobacterium animalis* AMT30 strain was expressed as a percentage of the number of *Bifidobacterium animalis* AMT30 after 180 minutes in the case of survivability determining at pH value of 3, and after 6 hours in the case of the number determination of *Bifidobacterium animalis* AMT30 in the presence of bile salts compared with the number of *Bifidobacterium animalis* AMT30 strain in the control

TABLE 3

Survivability of *Bifidobacterium animalis* AMT30 at pH = 3

| | number of bacteria (log10 cfu/ml) | | | | survivability |
|---|---|---|---|---|---|
| | before pH lowering | pH = 3 | | | after 180 minutes % |
| | 0 | 0 | 40 minutes | 180 minutes | |
| *Bifidobacterium animalis* AMT30 | 9.17 | 9.16 | 9.18 | 9.28 | 100 |

TABLE 4

Survivability of *Bifidobacterium animalis* AMT30 in the presence of 3% of bile salts

| | number of bacteria (log10 cfu/ml) | | | | | survivability after 6 h [%] |
|---|---|---|---|---|---|---|
| | before bile salts addition | after bile salts addition | | | | |
| | | 0 h | 1 h | 3 h | 6 h | |
| *Bifidobacterium animalis* AMT30 | 9.07 | 9.10 | 9.00 | 8.88 | 8.50 | 94 |

The examined strain of *Bifidobacterium animalis* AMT30 showed 100% of survivability at low pH=3 and 94% of survivability in the presence of bile salts in 3% concentration in the medium. The results showed high resistance of *Bifidobacterium animalis* AMT30 at low pH as well as in the presence of bile salts. This indicates that the *Bifidobacterium animalis* AMT30 strain adapts to the conditions of gastrointestinal tract.

Determination of *Bifidobacterium animalis* AMT30 Ability to Grow in the Presence of Selected Antibiotics Most Frequently Used in the Treatment of Animals Studies on the ability to grow of *Bifidobacterium animalis* AMT30 in the presence on 20 selected antibiotics were performed using shared cultures method. For this purpose Garche's liquid medium was inoculated with both *Bifidobacterium animalis* AMT30 in an amount of 4.9×10$^6$ colony forming units/ml and one of 20 antibiotics in concentration corresponding to an antibiotic dose used in animal treatment per kilogram of body weight. The culture was carried out in three parallel tubes under anaerobic conditions at 37° C. for 24 hours. In addition, parallel control culture of the studied strain without presence of selected antibiotics was carried out. The number of the live cells was determined directly after inoculation and after 24 hours. Incubation of bacteria on Petri dishes was carried out at 37° C. for 48 hours under anaerobic conditions (sealed jar with GasPack AN0025A cartridge, Oxoid). The results are presented in Table 5

TABLE 5

Determination of *Bifidobacterium animalis* AMT30 ability to grow in the presence of selected antibiotics most frequently used in the treatment of animals

| Active substance | Inoculum AMT30 [cfu/ml] | The number of *B. animalis* AMT30 after 24 hours of incubation [cfu/ml] |
|---|---|---|
| AMT30 control culture without antibiotic | 4.9 × 10$^6$ | 2.4 × 10$^9$ |
| Tiamulin 20.2 mg/kg b.w. | 4.9 × 10$^6$ | 7.6 × 10$^5$ |
| Enrofloxacin 10 mg/kg b.w. | 4.9 × 10$^6$ | 4.4 × 10$^4$ |
| Trimethoprim/sulfamethoxazole 100 mg + 50 mg/kg b.w. | 4.9 × 10$^6$ | 3.2 × 10$^6$ |
| Colistin 0.37 ml/10 kg b.w. | 4.9 × 10$^6$ | 1.9 × 10$^9$ |
| Florfenicol 20 mg/kg b.w. | 4.9 × 10$^6$ | 5.8 × 10$^5$ |
| Tilmicosin 20 mg/kg b.w. | 4.9 × 10$^6$ | 1.0 × 10$^6$ |
| Toltrazuril 7 mg/kg b.w. | 4.9 × 10$^6$ | 1.1 × 10$^9$ |
| Amprolium 20 mg/kg b.w. | 4.9 × 10$^6$ | 1.5 × 10$^9$ |
| Levamisole 25 mg/kg b.w. | 4.9 × 10$^6$ | 1.8 × 10$^9$ |
| Flubendazole 1.43 mg/kg b.w. | 4.9 × 10$^6$ | 1.4 × 10$^9$ |
| Doxycycline 50 mg/1 kg b.w. | 4.9 × 10$^6$ | 3.6 × 10$^5$ |
| Amoxicillin 20 mg/kg b.w. | 4.9 × 10$^6$ | 4.4 × 10$^5$ |
| Neomycin 20 mg/kg b.w. | 4.9 × 10$^6$ | 3.3 × 10$^7$ |
| Sodium sulfachloropyrazine 50 mg/kg b.w. | 4.9 × 10$^6$ | 2.4 × 10$^9$ |
| Amoxicillin + clavulanic acid 8 mg/kg b.w. | 4.9 × 10$^6$ | 1.8 × 10$^5$ |
| Phenoxymethylpenicillin 20 mg/kg b.w. | 4.9 × 10$^6$ | 8.0 × 10$^5$ |
| Lincomycin 5 mg/kg b.w. | 4.9 × 10$^6$ | 1.4 × 10$^3$ |
| Lincomycin + spectinomycin 150 mg of antibiotic activity/kg b.w. | 4.9 × 10$^6$ | 9.2 × 10$^4$ |
| Tylvalosin 40 mg/kg b.w. | 4.9 × 10$^6$ | 3.2 × 10$^5$ |
| Tylosin 100 mg/kg b.w. | 4.9 × 10$^6$ | 1.4 × 10$^6$ |

*Bifidobacterium animalis* AMT30 strain showed unique, broad spectrum of antibiotic resistance against studied antibiotics. Outstanding activity to multiply was found for AMT30 strain in the presence of 7 (Colistin, Toltrazuril, Amprolium, Levamisole, Flubendazole, Neomycin, Sodium sulfachloropyrazine) of the 20 studied antibiotics in relation to the number which the strain has reached in the control culture. However in the presence of Trimethoprim/sulfamethoxazole, Tilmicosin and Tylosin the number of *Bifidobacterium animalis* AMT30 remained at the level of inoculum. In the case of the cultures shared with Tiamulin, Enrofloxacin, Florfenicol, Amoxicillin, Doxycycline, Amoxycillin+ clavulanic acid, Phenoxymethylpenicillin, Licomycin and Tylvalosin decrease in the number of bacteria of AMT30 strain from 1 to 3 orders of magnitude in comparison to the control culture was recorded. *Bifidobacterium animalis* AMT30 showed also antibiotic resistance against the most frequently used antibiotics in poultry farming.

The invention claimed is:

1. A composition comprising a bacteria strain, medium and bulking agent, wherein the bacterial strain comprises a lyophilized strain of *Bifidobacterium animalis* AMT30, (PCM Accession No. B/00109) in an amount of 10$^3$ to 10$^{13}$ of colony forming units cfu/ml-g.

2. The composition of claim 1, wherein the composition is a cream, an ointment, a parapharmaceutical, a pharmaceutical, a food preparation or product, or a food and/or water additive for humans or animals.

* * * * *